United States Patent [19]

Kaufman

[11] 4,181,446

[45] Jan. 1, 1980

[54] PRE-OPERATIVE SURGICAL SCRUBBER

[76] Inventor: Jack W. Kaufman, 357 Frankel Blvd., Merrick, N.Y. 11566

[21] Appl. No.: 828,763

[22] Filed: Aug. 29, 1977

[51] Int. Cl.² .................... A46B 1/00; A46B 11/02; A47K 7/03
[52] U.S. Cl. ........................................ 401/9; 15/114; 15/187; 401/24; 401/28; 401/291
[58] Field of Search ............... 15/104.94, 114, 187, 15/188, 116 A, 119 A, 244 B, 244 C; 118/270; 401/19, 24, 28, 9; 220/339

[56] References Cited

U.S. PATENT DOCUMENTS

| | | | |
|---|---|---|---|
| 1,578,074 | 3/1926 | Chandler | 15/188 |
| 2,230,312 | 2/1941 | Sieb et al. | 15/105 |
| 2,752,623 | 7/1956 | Tupper | 15/111 |
| 2,795,807 | 6/1957 | Salvy | 15/187 X |
| 3,286,294 | 11/1966 | Raffe | 15/104.9 X |
| 3,295,904 | 1/1967 | Cobb | 220/339 X |
| 3,447,181 | 6/1969 | Coker et al. | 15/244 R X |
| 3,556,667 | 1/1971 | Kaufman | 401/28 |
| 3,606,919 | 9/1971 | Joerger et al. | 220/339 X |
| 3,704,072 | 11/1972 | Kaufman | 401/28 X |

FOREIGN PATENT DOCUMENTS 1223871 2/1960 France ........................ 15/187

*Primary Examiner*—Daniel Blum
*Attorney, Agent, or Firm*—Lackenbach, Lilling & Siegel

[57] ABSTRACT

A brush back having bristles on one face and being bendable to swing the bristles into oppositely extending relation for brushing engagement with an internal or concave surface.

4 Claims, 2 Drawing Figures

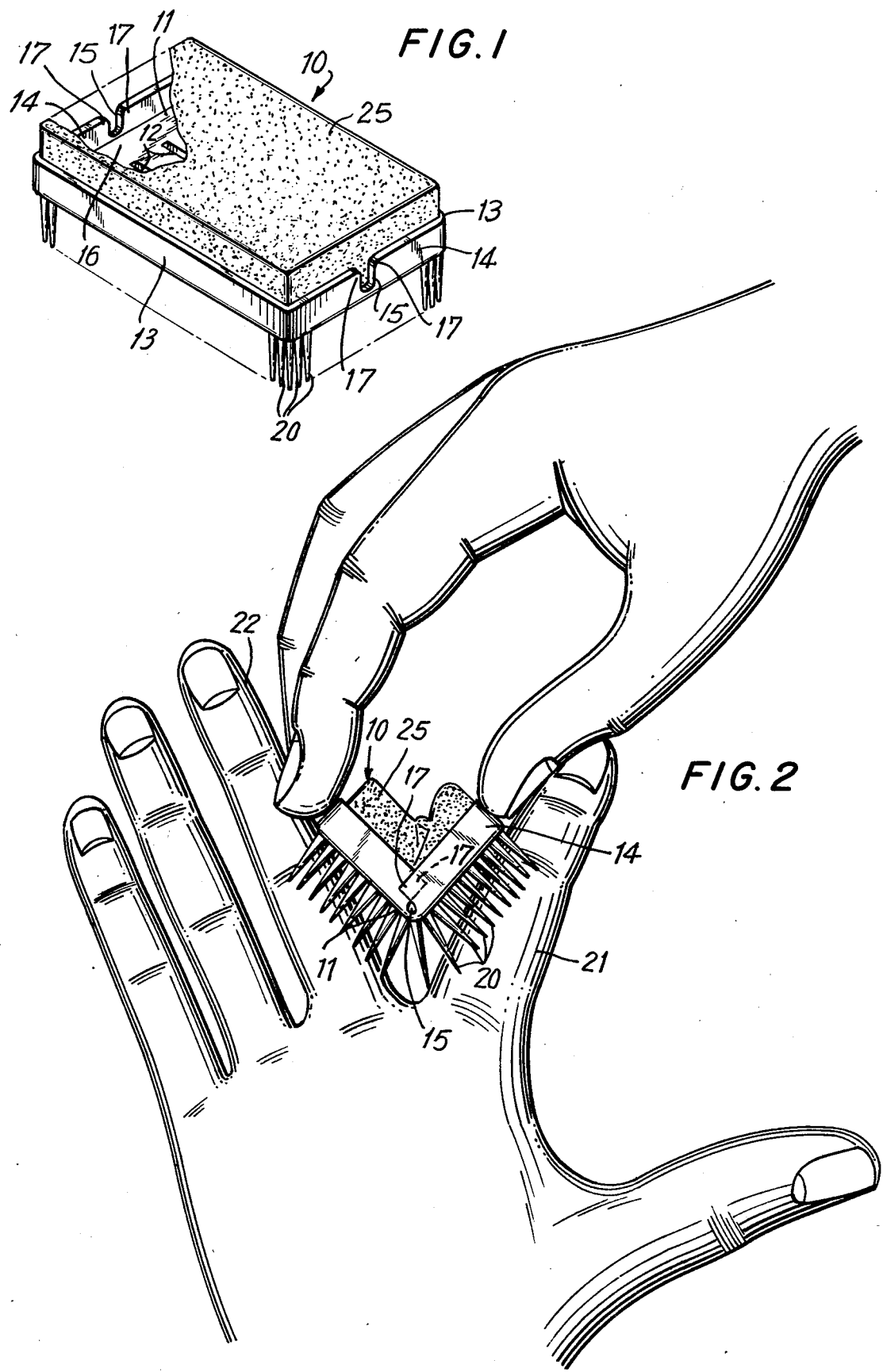

PRE-OPERATIVE SURGICAL SCRUBBER

BACKGROUND OF THE INVENTION

As is well known to those versed in the field of surgical scrub brushes and the like, the entry of such brushing devices into relatively small concave or internal regions presents some difficulty, as between fingers, especially of persons with small hands. Prior scrubbing devices do not perform well in such small concave regions, so that scrubbing action was not effective if existent at all.

SUMMARY OF THE INVENTION

It is, therefore, an important object of the present invention to provide a pre-operative surgical scrub brush which is uniquely well suited for entry into relatively small spaces or concavities, as between the user's fingers, to assure proper scrubbing action at such locations.

It is a futher object of the present invention to provide a brush construction of the type described in the preceding paragraph, which is well suited for use on internal or concave surfaces without sacrificing the scrubbing effectiveness on generally flat or convex surfaces, and is quickly and easily adaptable to all surface configurations by simple finger manipulation.

It is still another object of the present invention to provide a pre-operative scrub brush construction of the type described which is adapted for economic mass production to achieve cost savings economically justifying disposal after a single use, and which may incorporate scrubbing elements both in the nature of bristles and sponge with fluid communication therebetween for effective detergent, germicidal and/or disinfectant dispersion.

Other objects of the present invention will become apparent upon reading the following specification and referring to the accompanying drawings, which form a material part of this disclosure.

The invention accordingly consists in the features in construction, combinations of elements, and arrangements of parts, which will be exemplified in the construction hereinafter described, and of which the scope will be indicated by the appended claims.

BRIEF DESCRIPTION OF THE DRAWINGS

FIG. 1 is a top perspective view showing a brush construction of the present invention, partly broken away to illustrate internal structure.

FIG. 2 is an end view of the instant brush construction in operative association with a user's hands.

DESCRIPTION OF THE PREFERRED EMBODIMENT

Referring now more particularly to the drawings, and specifically to FIG. 1 thereof, a preoperative surgical scrubber or brush is shown therein and generally designated 10. The brush includes a generally flat plate or body 11 defining a brush back, which may be normally flat and of elongate, say rectangular outline configuration, but without limitation thereto. The normally flat brush back 11 may be formed with through openings or perforations, such as slots 12 extending generally longitudinally of the brush back. The openings or slots 12 may serve to pass soap or detergent and/or a disinfectant between opposite sides of the brush back, as will be more fully apparent hereinafter.

In practice, the normally generally flat brush back 11 may be fabricated of a suitable plastic material, say being self sustaining in its normally flat condition, and having flexibility enabling the brush back to be bent or folded upon itself, say to an obtuse angle when desired.

In the illustrated embodiment, the brush back 11 is of generally rectangular outline configuration, and provided on opposite side edges with upstanding longitudinal ribs or flanges 13. The longitudinal ribs or flanges 13 define upstanding side walls and effectively stiffen the brush back 11 against flexure or bending about a laterally extending or transverse axis.

Additionally, extending along each end edge of brush back 11 is an upstanding end wall, rib, or flange 14 extending between and integral at its opposite ends with the adjacent ends of side flanges 13. Each end rib or flange 14 may be notched, cut away or interrupted in a medial region, as at 15, notches 15 being generally aligned longitudinally of the brush back 11.

Thus, the ribs or flanges 13 and 14 combine to define a generally circumferential upstanding wall about the upper or outer face of brush back or plate 11. Further, the brush back 11 and the circumferential wall or flange 13, 14 may advantageously be integrally fabricated of plastic, as by suitable mass production techniques, say injection molding, or the like.

It will be appreciated that the circumferential flange or wall 13, 14 effectively stiffens or rigidifies the brush back 11 against flexure, except along a longitudinally medially extending region of the brush back between the notches or cut out 15. Thus, the longitudinally extending medial region 16 of brush back 11, between the notches 15, is bendable or foldable to swing the remaining portions of the brush back upwardly toward each other. In this condition, the adjacent flange portions 17 on opposite sides of each cut out 15 may swing into overlapping relation, as may be seen in FIG. 2.

In addition, on the underside of brush back 11, projecting downwardly and outwardly therefrom, generally normal thereto, are a multiplicity of projections or bristles 20. In practice, the bristles may be molded integral with and project in row from the undersurface of brush back 11, generally in the direction away from the upstanding circumferential flange 13, 14. While the bristles 20 are flexible, they generally move with the adjacent or contiguous portion of brush back 11, remaining generally normal thereto, so that certain bristles swing in angular relation with respect to other bristles. That is, the bristles 20 depending from the brush back 11 on one side of the medial longitudinal brush back region 16 swing in angular relation away from the bristles depending from the brush back region on the other side of the medial location. This condition is shown in FIG. 2, where it will be apparent that the brush back 11 has been folded to a considerable degree upon itself, so as to occupy less overall space for convenient entry into a relatively small concavity or internal space, as between adjacent fingers 21 and 22 of the user. It is by this highly efficient flexural action that the instant brush construction 10 is capable of effective brushing action in relatively small internal spaces or concavities, which were heretofore not accessible to conventional brush structures. However, it is understood that the instant brush construction sacrificies none of its brushing effectiveness on generally flat or convex surfaces, being usable thereon in its unflexed condition.

As described hereinbefore, the brush back 11, circumferential flange 13, 14 and bristles 20 may all be integrally molded, say of plastic, as a single unit for efficient and economical production. In addition, there may be provided or secured a rubbing pad or sponge 25 seated on the upper side or surface of brush back 11 conformably within the circumferential flange 13, 14. In the illustrated embodiment the rubbing pad or sponge 25 is of generally rectilinear configuration and snugly engaged within circumferential wall 13, 14 to be effectively retained thereby. If desired, the sponge or pad 25 may be impregnated with or otherwise carry a supply of soap or detergent, germicidal or antiseptic for dispersion therefrom to the surface being scrubbed, as directly from the sponge and through openings 12 to the bristles 20. The sponge or rubbing pad 25 is of a flexibility consistent with the desired manual flexibility of brush back 11, so that simultaneous flexure of both the brush back and sponge may be readily manually accomplished, as shown in FIG. 2, while the sponge may serve to enhance the restoring force, so that the brush back 11 returns with suitable rapidity to its generally flat planar condition.

From the foregoing, it is seen that the instant preoperative scrub brush is extremely simple in structure, durable and reliable in operation, economic to manufacture, and greatly facilitates entry into and scrubbing action within relatively small spaces or internal surface regions, such as between the fingers, for increased overall scrubbing effectiveness.

It should also be appreciated that the exterior surfaces of the ribs or flanges 13 may be suitably grooved (not shown) so as to facilitate gripping action by one's fingers.

Although the present invention has been described in some detail by way of illustration and example for purposes of clarity of understanding, it is understood that certain changes and modifications may be made within the spirit of the invention.

What is claimed is:

1. A brush construction comprising a generally planar brush back having opposite faces, and a multitude of integral bristles projecting from one face of said brush back, said brush back being self-sustaining in its normally flat condition and being fabricated of a plastic material having flexibility enabling said brush back to be bent or folded upon itself, and being provided with generally circumferential rib means defining upstanding side and end walls stiffening the brush back against bending, said rib means being absent only along a medial region to facilitate the bending of said brush back along said medial region to fold upon itself toward the other face of said brush back to swing said bristles into angular relation with each other for brushing engagement with an internal surface; and a resilient rubbing sponge secured on said other brush back face and conformably engageable within the upstanding side and end walls formed by said generally circumferential rib means; whereby the flexural action of the plastic material enabling the brush back to be restored to its unflexed condition, and whereby said sponge also serves to enhance the restoring of said brush back to its unflexed normally flat condition.

2. A brush construction according to claim 1, said brush back being bendable to an obtuse angle, said bristles being normally generally perpendicular to said brush back in general parallelism with each other and swingable on said bending to extend generally oppositely away from each other.

3. A brush construction according to Claim 1, said sheet being perforate to pass liquid.

4. A brush construction according to Claim 3, said rib means comprising longitudinal and end flanges on said other face of said sheet and being interrupted at oppositely spaced medial locations by notches cut out of the end flanges to facilitate bending of said brush back along the medial region thereof.

* * * * *